United States Patent [19]

Gandy et al.

[11] Patent Number: 5,242,932
[45] Date of Patent: Sep. 7, 1993

[54] TREATMENT OF AMYLOIDOSIS ASSOCIATED WITH ALZHEIMER DISEASE

[75] Inventors: Samuel E. Gandy; Gregg L. Caporaso; Paul Greengard, all of New York, N.Y.

[73] Assignee: The Rockefeller University, New York, N.Y.

[21] Appl. No.: 809,174

[22] Filed: Dec. 17, 1991

[51] Int. Cl.$^5$ .................. A01N 43/16; A01N 43/42; A61K 31/47
[52] U.S. Cl. ................ 514/313; 514/453; 514/468; 514/510; 514/691; 514/729; 514/739; 514/766
[58] Field of Search ............ 514/313, 453, 468, 510, 514/691, 729, 739, 766

[56] References Cited

U.S. PATENT DOCUMENTS

| 4,806,537 | 2/1989 | Roberts | 514/253 |
| 4,916,135 | 4/1990 | Effland et al. | 514/297 |
| 5,093,333 | 3/1992 | Saab | 514/314 |
| 5,102,892 | 4/1992 | Geiss et al. | 514/313 |

OTHER PUBLICATIONS

Caporaso et al. "Protein phosphorylation regulates secretion of Alzheimer β/A4 amyloid precursor protein", Proc. Natl. Acad. Sci., USA vol. 89, pp. 3055-3059, Apr. 1992.
Gandy et al., Alzheimer's Disease: New Therapeutic Approaches, Marcel Dekker, pp. 175-192 (1992), "A Cell Biological Approach to the Therapy of Alzheimer-Type Cerebral β/A4–Amyloidosis."
Gandy et al., ed. Alzheimer's Disease: Basic Mechanisms, Diagnosis and Therapeutic Strategies, John Wiley & Sons Ltd., (1991), Chapter 19, pp. 155-172, "Signal Transduction and the Pathobiology of Alzheimer's Disease".
Benowitz et al., Experimental Neurology, 106, pp. 237-250 (1989), "The Amyloid Precursor Protein is Concentrated in Neuronal Lysosomes in Normal and Alzheimer Disease Subjects."
Caporaso et al., Proc. Natl. Acad. Sci. U.S.A., 89, pp. 2252-2256 (Mar. 15, 1992), "Chloroquine Inhibits Intracellular Degradation But Not Secretion of Alzheimer β/A4 Amyloid Precursor Protein."
Cole et al., Neurochemical Research, 14(10), pp. 933-939 (1989), "Evidence for Lysosomal Processing of Amyloid-Protein Precursor in Cultured Cells."

Primary Examiner—Nathan M. Nutter
Attorney, Agent, or Firm—Klauber & Jackson

[57] ABSTRACT

Agents which modulate or affect the intracellular trafficking and processing of proteins in the mammalian cell can be utilized to affect the trafficking and processing of APP, thereby inhibiting production of Alzheimer type amyloidosis. Particularly useful agents are chloroquine and its related derivatives such as primaquine.

8 Claims, 6 Drawing Sheets

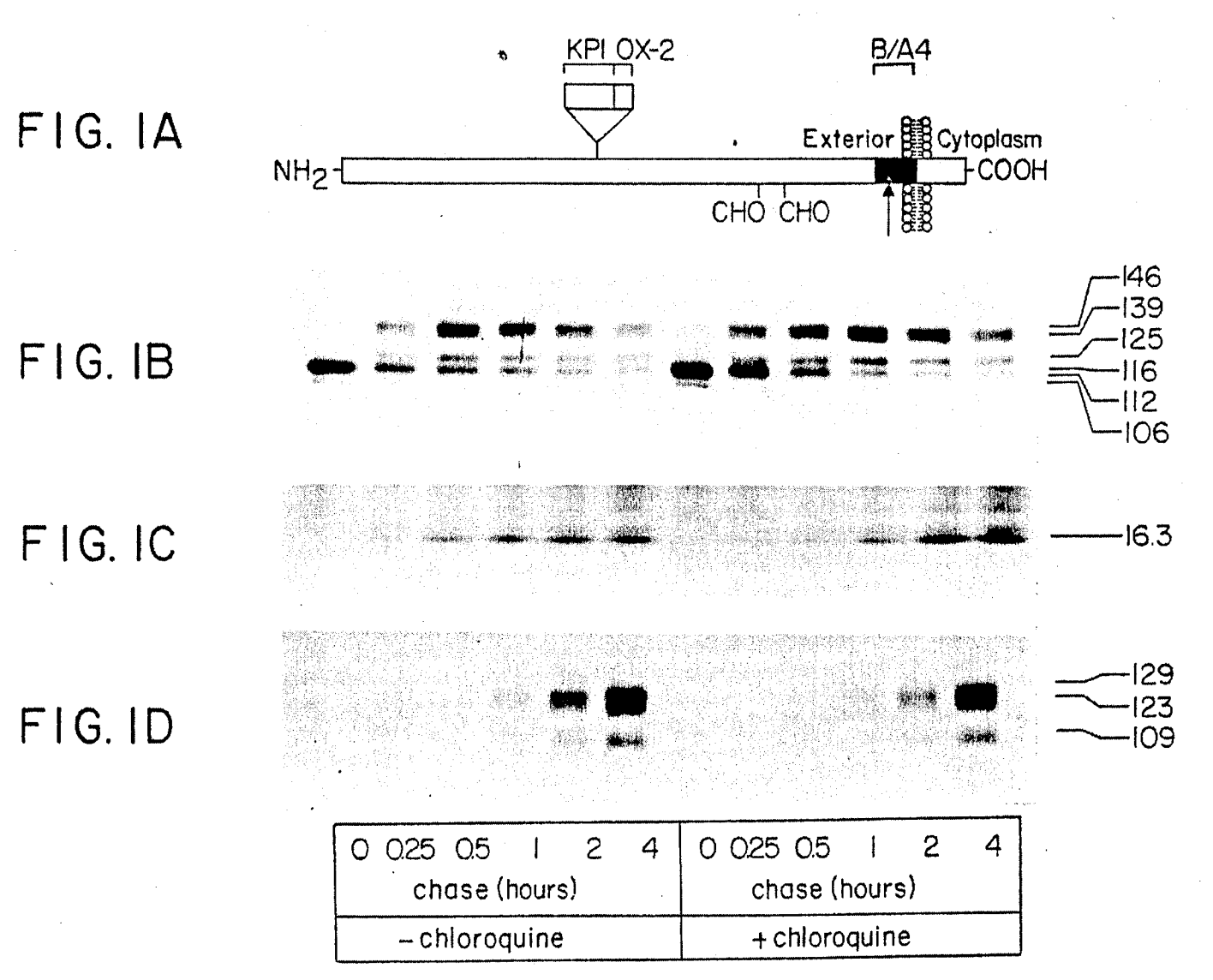

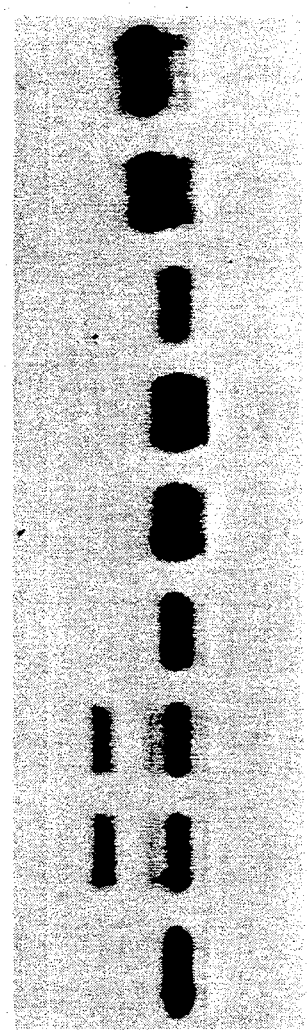
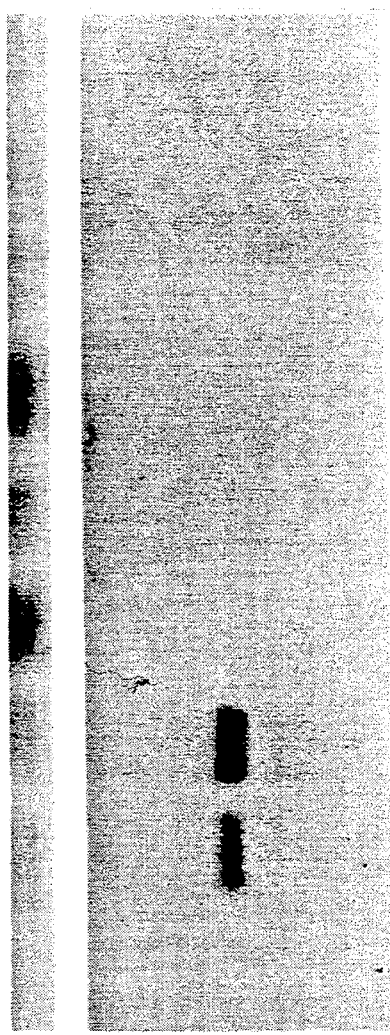
FIG. 6A  FIG. 6B  FIG. 6C

TREATMENT OF AMYLOIDOSIS ASSOCIATED WITH ALZHEIMER DISEASE

This invention was made with government support under Grant AGO9464 awarded by the National Institute of Health. The Government has certain rights in the invention.

BACKGROUND OF THE INVENTION

The leading cause of dementia and the fourth leading cause of death in the developed world is Alzheimer disease, which afflicts an estimated 10% of the population over 65 years of age in the United States. The disease manifests itself as insidious memory loss, cognitive decline, and personality changes that result in loss of functional ability over the course of a decade. In their debilitated state, patients usually retain only vegetative neurologic function, and succumb to secondary infections.

Alzheimer disease is characterized by certain neuropathological lesions, including intracellular neurofibrillary tangles and extracellular parenchymal and cerebrovascular amyloid. The principal component of the amyloid deposits is a protein designated $\beta/A4$ amyloid (4, 5), a ~4 kDa polypeptide arising from cleavage of the amyloid precursor protein (APP), see Goldgaber et al., *Science*, 235, pp. 887-880 (1987). APP exists as three major transmembrane isoforms ($APP_{695}$, $APP_{751}$, and $APP_{770}$) that result from alternative splicing of a single primary transcript (FIG. 1A), see Kang et al., *Nature* (London), 325, pp. 733-736 (1987). Proteolytic processing of APP leads to cleavage within the $\beta/A4$ domain and precludes amyloidogenesis. The biochemical defect responsible for amyloid production in Alzheimer disease might therefore involve either a deficiency in normal proteolysis or excessive activity of an alternative pathway. It is noteworthy that two types of inherited cerebral amyloidoses—hereditary cerebral hemorrhage with amyloidosis (Dutch type) and familial early onset Alzheimer disease—are associated with mutations in the coding sequence of APP near the $\beta/A4$-amyloid domain. Alzheimer disease is characterized by abnormal protein phosphorylation and altered protein catabolism. From the work of several laboratories, altered protein phosphorylation has been implicated in the formation of the intracellular neurofibrillary tangles found in Alzheimer disease. However, a role for protein phosphorylation in the catabolism of the $\beta/A4$ protein precursor ($\beta APP$) has not been demonstrated.

A central feature of the pathology of Alzheimer disease is the deposition of amyloid protein within plaques. The 4 kDa amyloid protein (also referred to as A4 (APC, $\beta$-amyloid or BAP) is a truncated form of the larger amyloid precursor protein (APP) which is encoded by a gene localized on chromosome 21 (Goldgaber et al., 1987, *Science*, 235:877-880; Kang et al., 1987, *Nature*. 325:733-736) Jenkins et al., 1988, *Biochem. Biophys. Res. Commun.*, 151:1-8; Tanzi et al., 1987, *Science*. 235:880-885). Genetic linkage analysis, using DNA probes that detect restriction fragment length polymorphisms (RFLPS, Botstein et al., 1980, *Am. J. Hum. Genet.*, 32:314-331), has resulted in the localization of a candidate gene (FAD, familia Alzheimer disease) on human chromosome 21 in families with high frequencies of Alzheimer's disease (St. George-Hyslop et al., 1987, *Science*, 235:885-890). However, the FAD locus has not been localized precisely, and very little is known about its function. Initial studies of individuals with Down's Syndrome (DS), caused by trisomy of chromosome 21, indicate that these individuals develop Alzheimer-like pathology beyond the second decade of life. However, analysis of multiple Alzheimer pedigrees revealed that the APP gene does not segregate with familial Alzheimer disease (Van Broackhoven et al., 1987, *Nature*. 328:153-155; Tanzi et al., 1987, *Nature,* 329:156-157). Furthermore, two recent studies with new families demonstrated the absence of a linkage of chromosome 21 markers to familial Alzheimer disease (Schellenberg et al , 1988, 241:1507-1510; Rosea et al., 1988, *Neurology*, 38:173).

Age, genetic elements, and, possibly environmental factors appear to contribute to cellular pathology of Alzheimer's disease. A fundamental but unanswered question in the pathogenesis of Alzheimer disease is the relationship between abnormalities of neurons and the deposition of amyloid. Specifically, the cellular origin of pathological events leading to the deposition of amyloid fibrils adjacent to some areas of the blood-brain barrier (cerebrovascular amyloid) and in the proximity of nerve terminals (neuritic plaques) in specific brain regions as well as extracellular amyloid in plaques cores is not known. Glenner and Wong have described the purification and characterization of meningeal amyloid from both brains of individuals with Alzheimer disease (Glenner and Wong, 1984, *Biochem. Biophys. Res. Commun.*, 120:885-890) or Down's Syndrome (Glenner & Wong, 1984, *Biochem. Biophys. Res. Comm.*, 122:1131-1135) and determined the N-terminal peptide sequences. Among 24 residues analyzed, the two amyloid peptides showed only one difference, namely at amino acid position 11 (glutamine in Alzheimer disease amyloid, versus glutamic acid in Down's Syndrome amyloid) among 24 residues analyzed. Subsequent studios of amyloid from Alzheimer brain plaque cores revealed amino acid sequences identical to the reported Down's Syndrome cerebrovascular amyloid data (Masters et al, 1985, *Proc. Natl. Acad. Sci., U.S.A.,* 82:4245-4249). Copy-DNA analysis of APP transcripts form both normal tissue and Alzheimer brain material demonstrated the presence of the codon for glutamic acid at this position (Kang et al., 1987, supra; Goldgaber et al, 1987, supra; Robakis et al., supra; Tanzi et al., 1987, *Science*, 235:880-884; Zain et al., 1988, *Proc. Natl. Acad. Sci., U.S.A.,* 85:929-933; Vitek et al., 1988, *Mol. Brain Res.,* 4:121-131).

Cerebral $\beta/A4$-amyloidosis is characteristic of several apparently related human conditions: Alzheimer's disease, Down's syndrome, hereditary cerebral hemorrhage with amyloidosis, Dutch type, and, to a lesser extent, normal aging. Like other organ-specific amyloidoses, the pathology of these conditions includes the accumulation of extracellular protein precipitates which form $\beta$-pleated sheets and bind Congo red dye (Cotran et al., "Robbin's Pathologic Basis of Disease," 4th ed., WB Saunders, Pa., 1984). Unlike other amyloidoses, however, in which the deposited peptide seems clearly derived from a hydrophilic domain in a circulating serum precursor, deposited $\beta/A4$-amyloid includes a portion of the intramembranous domain of an integral transmembrane protein, the Alzheimer $\beta/A4$ amyloid precursor protein (APP). This raises several novel questions about how APP is processed within the cell and about how $\beta/A4$ is released into the extracellular space. Synthetic $\beta/A4$ spontaneously aggregates and precipitates (15), thus demonstrating that the primary amino acid sequence of this domain of APP encodes sufficient structural information to determine its amyloidogenicity.

SUMMARY OF THE INVENTION

This invention relates to the use of agents which modulate or affect the intracellular trafficking and processing of APP, thereby inhibiting production of Alzheimer type amyloidosis. More particularly, the present invention concerns a method of inhibiting the production of Alzheimer type amyloidosis in a mammal comprising administering to the mammal an effective amount of at least one trafficking inhibitor of proteins, the inhibitor capable of decreasing the trafficking and processing of APP in the mammalian cell.

The present invention also relates to a treatment of amyloidosis associated with Alzheimer disease in a mammalian patient comprising administering to the patient an effective amount of at least one agent capable of inhibiting the trafficking and processing of APP.

The present invention also relates to a method for screening for agents that modulate amyloid formation comprising contacting mammalian cells with an agent suspected of being capable of modulating the trafficking and processing of APP and detecting for alterations in the trafficking and processing of APP.

BRIEF DESCRIPTION OF THE DRAWINGS

FIG. 1A is a schematic diagram of the APP molecule;

FIGS. 1B, 1C and 1D are autoradiograms of APP species immunoprecipitated from [$^{35}$S]methionine labeled PC12 cells in the presence or absence of chloroquine;

FIGS. 6A, 6B and 6C are autoradiograms of APP species immunoprecipitated from [$^{35}$S]methionine-labeled PC12 cells in the absence or presence of monensis, or brefeldin A.

DETAILED DESCRIPTION OF THE DRAWINGS

FIG. 1. (A) Schematic diagram of APP molecule showing extracellular, transmembrane, and cytoplasmic regions: $\beta$/A4 amyloid domain (shaded); normal intra-$\beta$/A4 amyloid cleavage site (15) (arrow); domain inserts for APP$_{751}$ (KPI only) and A-PP$_{770}$ (both KPI and OX-2) isoforms; and putative N-glycosylation sites (CHO). (B, C, and D) Autoradiograms of APP species immunoprecipitated from [$^{35}$S]methionine-labelled PC12 cells incubated during the chase period for 0, 0.25, 0,5, 1,,-2, or 4 h in the absence (left) or presence (right) of chloroquine. (B) APP holoproteins of 106, 112, 116, 125, 139, and 146 kDa presenting immature APP$_{695}$, APP$_{751}$, and APP$_{770}$ and mature APP$_{695}$, APP$_{751}$, and APP$_{770}$, respectively, in cell lysates. (C) 16.3 kDa peptide representing the normal carboxyl-terminal APP, fragment resulting from intra-$\beta$/A4 amyloid cleavage in cell lysates. (D) APP aminoterminal peptides of 109, 123, and 129 kDa representing secreted fragments of APP$_{695}$>, APP$_{751}$, and APP$_{770}$, respectively, in conditioned medium. Autoradiograms are from a single experiment analyzed either on a 4-15% continuous gradient SDS-polyacrylamide gel (B, top portion of film; C, bottom portion of film) or on a 6% SDS-polyacrylamide gel (D). Autoradiograms were exposed for different lengths of time to optimize signal clarity.

Figure 2A:
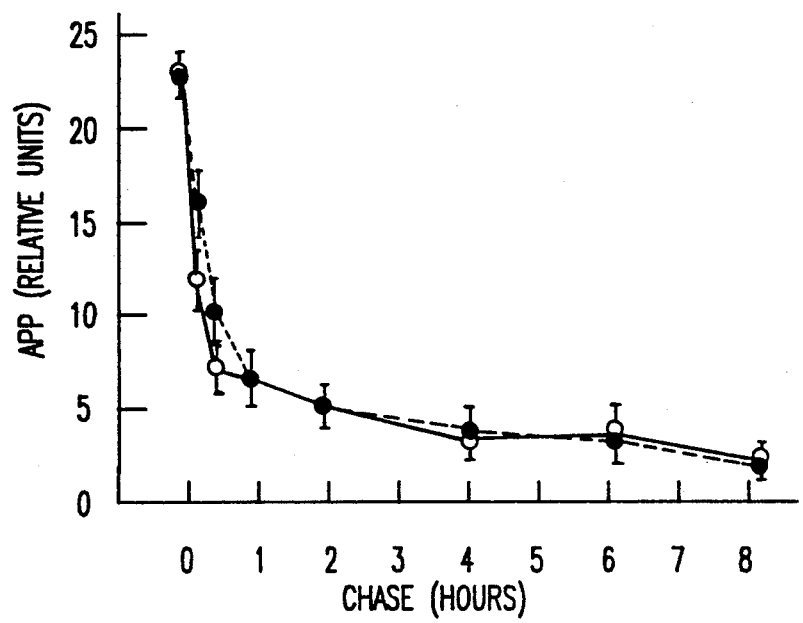
FIGS. 2A and 2B are graphs showing the recovery of immature APP in the absence or presence of chloroquine.
Figure 2B:
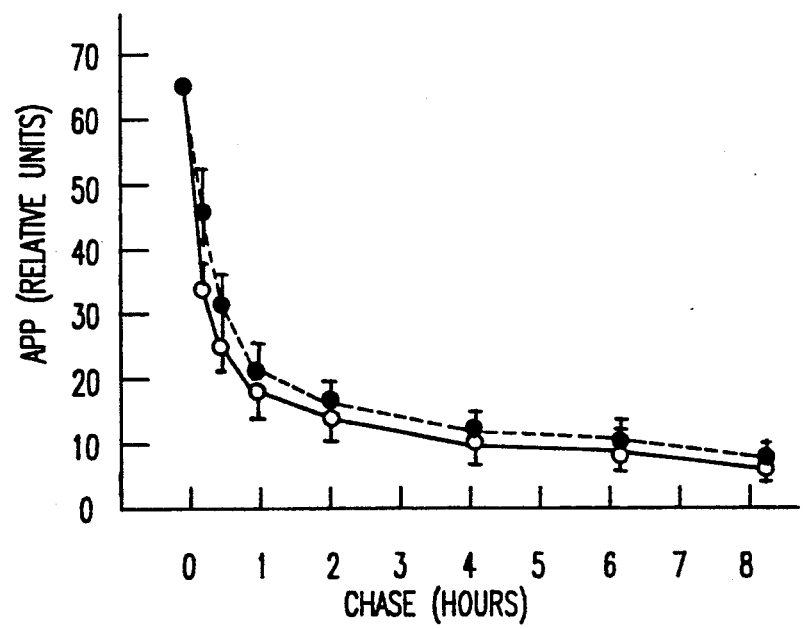

FIG. 2. Recovery of immature APP in the absence (open circles) or presence (filled diamonds) of chloroquine. (A) Immature APP$_{695}$. (B) Immature APPKPI (APP$_{751}$ and APP$_{7770}$) Results are means ±SEM of seven experiments; n=3 to 7 for individual time points. There was no statistically significant difference between untreated and treated samples (Student's unpaired t-test).

Figure 3A:
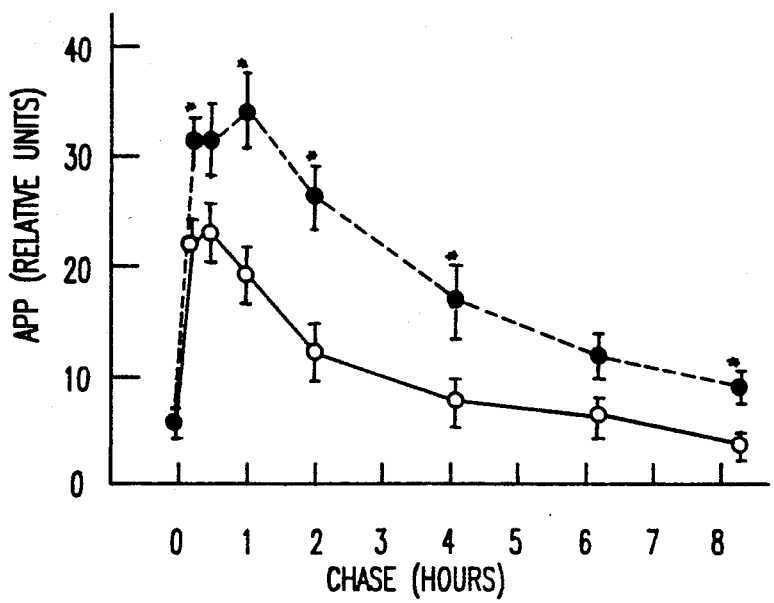
FIGS. 3A, 3B and 3C are graphs showing the recovery of mature APP in the absence or presence of chloroquine.
Figure 3B:
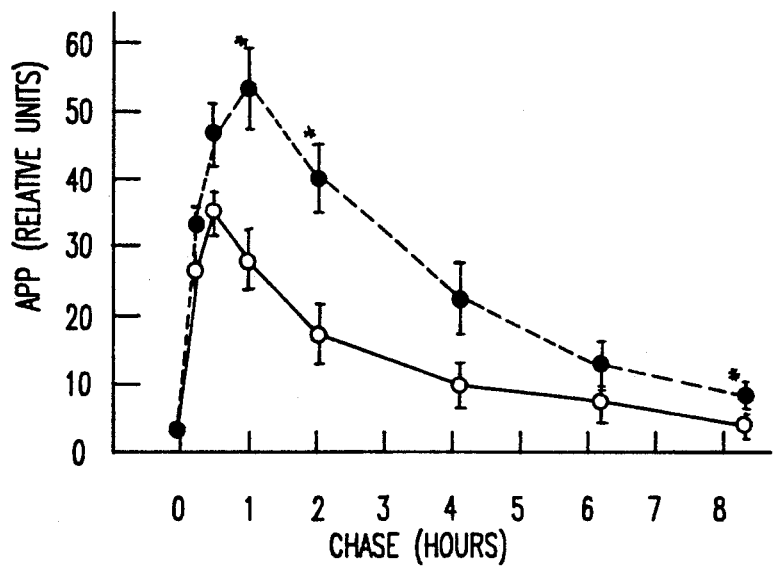
Figure 3C:
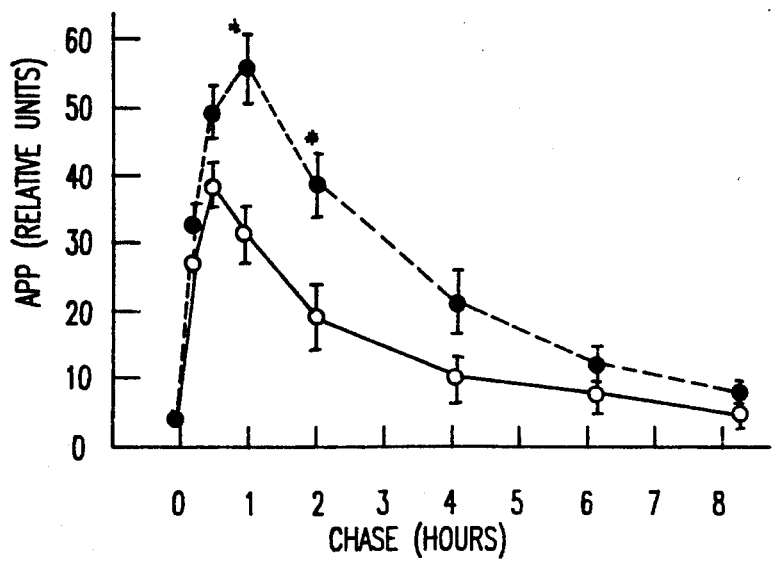

FIG. 3. Recovery of mature APP in the absence (open circles) or presence (filled diamonds) of chloroquine. (A,) Mature APP$_{695}$. (B) Mature APP$_{751}$, (C) Mature APP$_{770}$. Results are means ±SEM of seven experiments; n=3 to 7 for individual time points. Statistical significance between untreated and treated samples for individual time points was determined by Student's unpaired t-test (*, p<0.05).

Figure 4A:
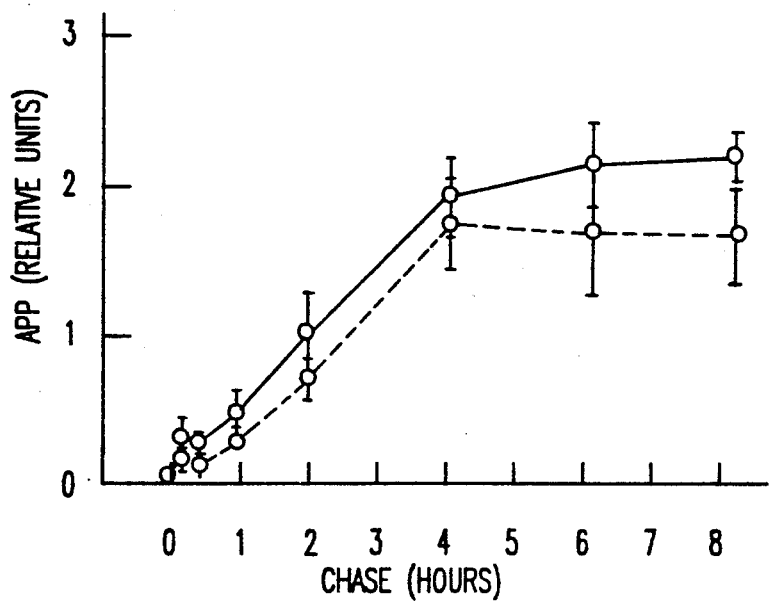
FIGS. 4A, 4B and 4C are graphs showing the recovery of secreted APP fragments in the absence or presence of chloroquine.
Figure 4B:
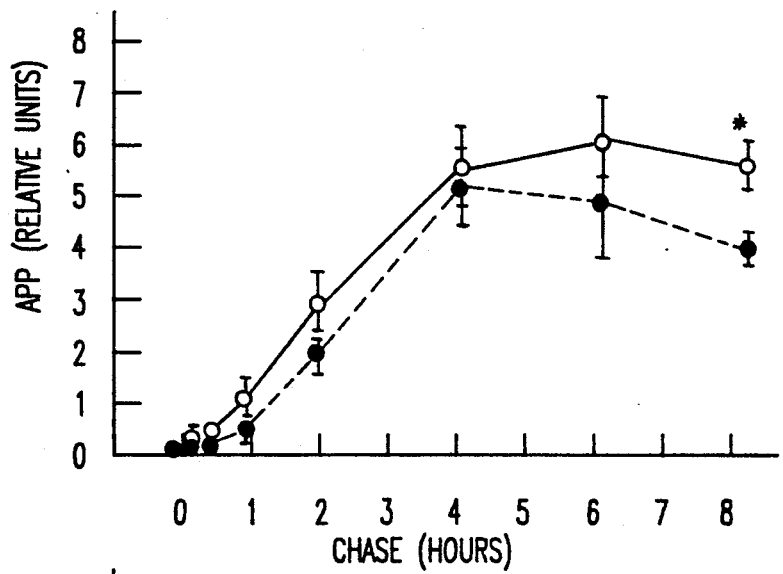
Figure 4C:
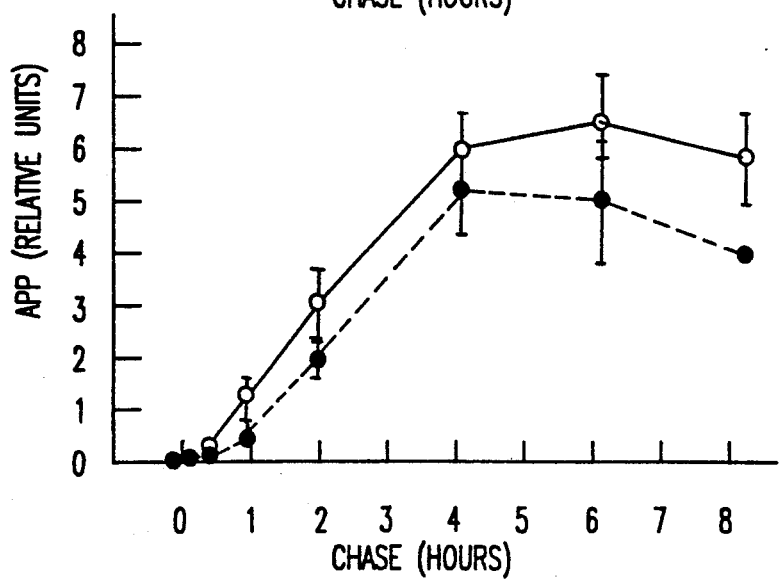

FIG. 4. Recovery of secreted APP fragments in the absence (open circles) or presence (filled diamonds) of chloroquine. (A) Secreted APP$_{695}$. (B) Secreted APP$_{751}$. (C) Secreted APP$_{770}$. Results are means ±SEM of seven experiments; n=3 to 7 for individual time points. Statistical significance between untreated and treated samples for individual time points was determined by Student's unpaired t-test (*, p<0.05).

Figure 5:
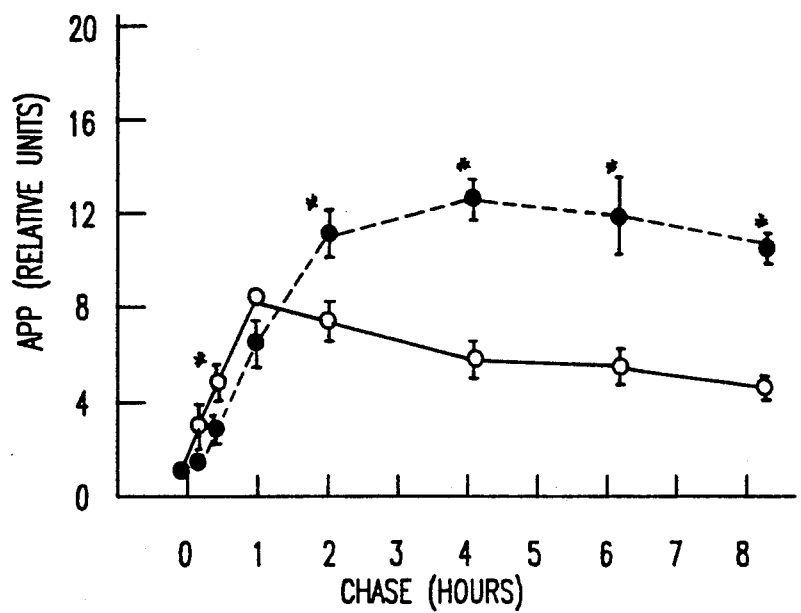
FIG. 5 is a graph showing the recovery of the 16.3 kDa carboxyl-terminal APP fragments in the absence or presence of chloroquine.

FIG. 5. Recovery of the 16.3 kDa carboxyl-terminal APP fragment in the absence (open circles) or presence (filled diamonds) of chloroquine. Results are means ±SEM of seven experiments; n=3 to 7 for individual time points. Statistical significance between untreated and treated samples for individual time points was determined by Student's unpaired t-test (p<0.05).

FIG. 6. Autoradiograms of APP species immunoprecipitated from [$^{35}$S]methionine-labelled PC12 cells incubated during preincubation, pulse, and chase periods of 0, 2, or 4 h in the absence (left) or presence of monensin (center) or brefeldin A (right). (A and B) Cell lysates. (C) Conditioned medium. (A) APP holoproteins of 106, 112, 116, 125, 139, and 146 kDa representing immature APP$_{695}$, APP$_{751}$, and APP$_{770}$ and mature APP$_{695}$, APP$_{751}$, and APP$_{770}$, respectively. (B) 16.3 kDa peptide representing the carboxyl-terminal APP fragment resulting from intra-$\beta$/A4 amyloid cleavage. (C) APP amino-terminal peptides of 109, 123, and 129 kDa representing secreted fragments of APP$_{695}$, APP$_{751}$, and APP$_{770}$, respectively.

DETAILED DESCRIPTION OF THE INVENTION

APP is synthesized as an integral transmembrane protein, probably on membrane-bound ribosomes or rough endoplasmic reticulum (ER) to allow for cotranslational insertion into the vesicle lumen. Such membrane vesicles typically contain a signal sequence receptor, which recognizes a hydrophobic signal sequence on the NH$_2$-terminus of the nascent polypeptide chain, and an intraluminal (intravesicular) signal peptidase activity, which cleaves off the hydrophobic signal peptide. Such a signal peptide sequence is present at residues 1-17 of nascent APP. Direct sequencing of the NH$_2$-terminus of secreted APP has revealed that the first residues are LEVPT (one-letter amino acid code; Palmert et al., *Proc. Natl. Acad. Sci. USA*, 86, 6338–6342, 1989), corresponding to predicted residues 18–22 of APP, and consistent with the predicted NH$_2$-terminal sequence following cleavage of the signal peptide.

Following synthesis, the APP polypeptide is subjected to several posttranslational modifications. In the Golgi, sulfate groups and carbohydrates are added to the extracellular or intraluminal domain. Sulfate is added to tyrosyl residues, and consensus sequence data suggest that the modified residue(s) may be tyrosine$^{217}$ and/or tyrosine$^{262}$. N-glycosylation may occur at residues 467–469 and 496–498. O-glycosylation may also occur, but the glycosylation site has not been localized (9, 21). Phosphate groups are also added to APP, presumably in its cytoplasmic domain, since protein phosphorylation enzymes (protein kinases) are typically intracellular in location.

These posttranslational modifications may offer some clues about the biology of APP. Tyrosine sulfation typically occurs in the domains of proteins which are destined to be released from the cell. This has proven to be the case for APP: following a short cellular half-life, the tyrosine sulfated ectodomain is released into the medium of cultured cells. Covalently attached sugar side groups are typical of the ectodomains of cell-surface proteins; indeed, a population of apparently full-length APP holoprotein can be detected on the surface of transfected cells.

Phosphorylation of a substrate protein frequently gives clues about the biology of that protein. Changes in the phosphorylation state of a protein can produce dramatic changes in the trafficking, processing, or biological activity of the protein. Certain cell-surface receptors are phosphorylated in their cytoplasmic domains as a mechanism of modifying sensitivity to ligand-induced effects. Cell adhesion molecules (CAMs) and extracellular matrix receptors are phosphorylated in their cytoplasmic domains, and the state of phosphorylation of CAMs may regulate interactions with the cytoskeleton. Endocytosis of the epidermal growth factor (EGF) receptor and interleukin-2 (IL-2) receptor is induced by protein kinase C-mediated phosphorylation in their respective cytodomains, at residues near the transmembrane domain. Of note, an APP phosphorylation site is rapidly phosphorylated by protein kinase C or calcium/calmodiulin-dependent protein kinase II and, like the protein kinase C phosphorylation site on IL-2R or EGFR, is located within 10 residues of the plasma membrane.

Recent evidence (Buxbaum et al., *Proc. Natl. Acad. Sci. USA*, 87, pp. 6003–6006, 1990) demonstrates directly that protein phosphorylation modulates an important event in the biology of APP, i.e., its proteolytic processing. In pulse-chase studies using PC12 cells, phorbol esters (drugs which stimulate protein kinase C) dramatically diminished recovery of mature APP while enhancing recovery of a COOH-terminal fragment of approximately 15 kDa. Okadaic acid (a drug which inhibits protein phosphatases 1 and 2A) had similar effects. When both phorbol ester and okadaic acid were simultaneously applied to cells, in addition to the effects of mature APP and the 15-kDa COOH-terminal fragment, a larger ($\sim$19 kDa) COOH-terminal fragment was generated in elevated amounts. In other experiments, H-7 (an inhibitor of protein kinases including protein kinase C) led to an apparent decrease in the basal rate of processing of APP, supporting the physiological significance of modulation of APP processing by protein kinase C. These results provide the first direct evidence for regulation of the rate of APP processing by protein phosphorylation. They also raise the possibility that protein phosphorylation can lead to an alternative, i.e. qualitatively different, pathway of APP processing.

The intracellular trafficking pathways involved in APP processing have begun to attract attention, but much remains to be clarified. Following its departure from the trans-Golgi, APP has been localized at two sites: Apparently intact APP holoprotein is detectable on the cell surface (Weidemann et al., *Cell*, 57. pp. 115–126, 1989); and a truncated soluble protein, containing the NH$_2$-terminal region of the molecule, is released from the cell (Ibid.). The cellular location at which APP is cleaved to produce the truncated soluble protein is unknown, but likely candidates include the Golgi, the lysosomal compartment, and/or the cell surface. Several lines of evidence suggest that the lysosome is likely to be one way station of APP during its intracellular itinerary. Neuronal lipofuscin, formed by the age-dependent accumulation of incompletely degraded lysosomal by-products, is characterized by the presence of APP-like immunoreactivity in association with intracellular vesicular lipofuscin granules. Using immunocytochemistry of brain, APP-like immunoreactivity appears as an intracellular vesicular staining pattern, interpreted as possibly representing association of APP immunoreactivity with lysosomes. Various protease inhibitors, including the lysosome acidification inhibitors ammonium chloride and chloroquine, have been suggested to slow APP processing (Cole et al., *Neurochem. Res.*, 14, 933–939, 1989). A signal sequence, asparagineproline-X-tyrosine has recently been identified. It is believed to target transmembrane proteins (including the low-density lipoprotein receptor, EGF receptor, and insulin receptor) to coated pits to initiate their endocytosis. These converging lines of evidence strongly suggest that at least some step in APP processing may occur in lysosomes. Such evidence would not necessarily preclude cell surface cleavage or the possibility that lysosomal residence occurs late in trafficking of COOH-terminal APP fragments rather than in the initial processing of APP holoprotein. Likewise, one cannot discern from the data currently available whether the proposed early lysosomal residence occurs after residence at the cell surface or along a pathway that delivers APP directly to the lysosome after it emerges from the trans-Golgi.

Cultured mammalian cells provide a readily accessible and well-characterized system for studies of protein trafficking. In the present invention, APP intracellular trafficking and processing by pulse-labelling PC12 neuroendocrine cells in the presence of various pharmacologic agents have been examined.

Utilizing such a screening method, agents which modulate or affect the trafficking and processing of APP, thereby inhibiting production of Alzheimer type amyloidosis, have been identified.

The following is not meant to be a complete or exhaustive list, but merely representative examples of the present invention:

7-chloro-4,4-diethylamino-1-methylbutylamino) quinoline (chloroquine);

8-(4-amino-1-methylbutylamino)-6-methoxyquinoline (primaquine);

4-(5'-diethylaminopentyl-2'-amino)-7-chloroquinoline;
4-diethylaminobutylamino-7-chloroquinoline;
4-(5'-diethylaminopentyl-2'-amino)-7-methylquinoline;
4-[5'-diethylaminopentyl-(2,)-amino]-7-iodoquinoline;
3-methyl-4-(5'-diethylaminopentyl]-2'-amino)-7-chloroquinoline;
4-(5'-diethylaminopentyl-2'-amino-5,7-dichloroquinoline;
3-ethoxy-4-(5-diethylaminopentyl-2'-amino)-7-chloroquinoline; [tetrahydro-6-hydroxy-6-(hydroxymethyl)-3,5-dimethyl-2H-pyran-2-yl]-2-furyl]-2-furyl]-9-hydroxy-β-methoxy-α,τ,2,8-tetramethyl-1,6-dioxaspiro[4.5]decane-7-butyric acid (monensin);
ammonium chloride;
methylamine; and
brefeldin A.

It is to be understood that derivatives and analogs of the above agents are also encompassed by the present invention.

Other agents known to modulate and affect the trafficking of proteins in cells are likewise utilizable in the present invention.

The agents for use in the present invention can be administered as a medicament, i.e., a pharmaceutical composition.

The pharmaceutical compositions used in the methods of this invention for administration to animals and humans comprise an active agent in combination with a pharmaceutical carrier or excipient.

The medicament can be in the form of tablets (including lozenges and granules), dragees, capsules, pills, ampoules or suppositories comprising a compound of the invention.

"Medicament" as used herein means physically discrete coherent portions suitable for medical administration. "Medicament in dosage unit form" as used herein means physically discrete coherent units suitable for medical administration, each containing a daily dose or a multiple (up to four times) or a sub-multiple (down to a fortieth) of a daily dose of the active compound of the invention in association with a carrier and/or enclosed within an envelope. Whether the medicament contains a daily dose, or for example, a half, a third or a quarter of a daily dose will depend on whether the medicament is to be administered once or, for example, twice three times or four times a day, respectively.

Advantageously, the compositions are formulated as dosage units, each unit being adapted to supply a fixed dose of active ingredients. Tablets, coated tablets, capsules, ampoules and suppositories are examples of preferred dosage forms according to the invention. It is only necessary that the active ingredient constitute an effective amount, i.e., such that a suitable effective dosage will be consistent with the dosage form employed in single or multiple unit doses. The exact individual dosages, as well as daily dosages, will of course be determined according to standard medical principles under the direction of a physician or veterinarian.

The active agent can also be administered as suspensions, solutions and emulsions of the active compound in aqueous or non-aqueous diluents, syrups, granulates or powders.

Diluents that can be used in pharmaceutical compositions (e.g., granulates) containing the active compound adapted to be formed into tablets, dragees, capsules and pills include the following: (a) fillers and extenders, e.g., starch, sugars, mannitol and silicic acid; (b) binding agents, e.g., carboxymethyl cellulose and other cellulose derivatives, alginates, gelatine and polyvinyl pyrrolidone; (c) moisturizing agents, e.g., glycerol; (d) disintegrating agents, e.g., agar-agar, calcium carbonate and sodium bicarbonate; (e) agents for retarding dissolution, e.g., paraffin; (f) resorption accelerators, e.g., quaternary ammonium compounds; (g) surface active agents, e.g., cetyl alcohol, glycerol monostearate; (h) adsorptive carriers, e.g., kaolin and bentonite; (i) lubricants, e.g., talc, calcium and magnesium stearate and solid polyethylene glycols.

The tablets, dragees, capsules and pills comprising the active agent can have the customary coatings, envelopes and protective matrices, which may contain opacifiers.

They can be so constituted that they release the active ingredient only or preferably in a particular part of the intestinal tract, possibly over a period of time. The coatings, envelopes and protective matrices may be made, for example, from polymeric substances or waxes.

The active ingredient can also be made up in microencapsulated form together, with one or several of the above-mentioned diluents.

The diluents to be used in pharmaceutical compositions adapted to be formed into suppositories can, for example, be the usual water-soluble diluents, such as polyethylene glycols and fats (e.g., cocoa oil and high esters, (e.g., $C_{14}$-alcohol with $C_{16}$-fatty acid]) or mixtures of these diluents.

The pharmaceutical compositions which are solutions and emulsions can, for example, contain the customary diluents (with, of course, the above-mentioned exclusion of solvents having a molecular weight below 200, in the presence of a surface-active agent), such as diluents, dissolving agents and emulsifiers. Specific nonlimiting examples of such diluents are water, ethyl alcohol, isopropyl alcohol, ethyl carbonate, ethyl acetate, benzyl alcohol, benzyl benzoate, propylene glycol, 1,3-butylene glycol, dimethylformamide, oils (for example, ground nut oil, glycerol, tetrahydrofurfuryl alcohol, polyethylene glycols and fatty acid esters of sorbitol or mixtures thereof.

For parenteral administration, solutions and suspensions should be sterile, e.g., water or arachis oil contained in ampoules and, if appropriate, blood-isotonic.

The pharmaceutical compositions which are suspensions can contain the usual diluents, such as liquid diluents, e.g., water, ethyl alcohol, propylene glycol, surface active agents (e.g., ethoxylated isostearyl alcohols, polyoxyethylene sorbitols and sorbitan esters), polycrystalline cellulose, aluminum methahydroxide, agar-agar and tragacanth, or mixtures thereof.

The pharmaceutical compositions can also contain bulking agents and preservatives, as well as perfumes and flavoring additions (e.g., peppermint oil and eucalyptus oil, and sweetening agents, (e.g., saccharin and aspartame).

The pharmaceutical compositions will generally contain from 0.5 to 90% of the active ingredient by weight of the total composition.

In addition to the active agent, the pharmaceutical compositions and medicaments can also contain other pharmaceutically active compounds.

Any diluent in the medicaments of the present invention may be any of those mentioned above in relation to the pharmaceutical compositions. Such medicaments may include solvents of molecular weight less than 200 as the sole diluent.

It is envisaged that this active compound will be administered perorally, parenterally (for example, intramuscularly, intraperitoneally, subcutaneously, transdermally or intravenously), rectally or locally, preferably orally or parenterally, especially perlingually, or intravenously.

The dosage rate, e.g., 0.05 to 20 mg/kg of body weight, will be a function of the nature and body weight of the human or animal subject to be treated, the individual reaction of this subject to the treatment, type of formulation in which the active ingredient is administered, the mode in which the administration is carried out and the point in the progress of the disease or interval at which it is to be administered. Thus, it may in some case suffice to use less than a minimum dosage rate, while other cases an upper limit must be exceeded to achieve the desired results. Where larger amounts are administered, it may be advisable to divide these into several individual administrations over the course of the day.

In a further embodiment of the present invention, the screening techniques utilized herein can be utilized as a means of identifying further agents which modulate or inhibit the production of Alzheimer type amyloidosis.

In this screening method, mammalian cells are contacted with an agent suspected of being capable of modulating the trafficking and processing of APP, and then examined for alterations in the trafficking and processing of APP.

EXAMPLES

Chloroquine was purchased from Sigma Chemical Company, monensin was purchased from Calbiochem, and brefeldin A was purchased from Epicentre Technologies (Madison, Wis.). Ascites fluid from mice injected intraperitoneally with hybridoma cells producing the anti-amino terminal APP monoclonal antibody 22Cll was the kind gift of R. P. Fracasso (Molecular Therapeutics, Inc., West Haven, Conn.) and T. V. Ramabhadran (The Rockefeller University Laboratory of Molecular and Cellular Neuroscience), and of S. S. Sisodia (The Johns Hopkins University School of Medicine, Baltimore, Md.). Affinity-purified rabbit anti-carboxyl terminal APP antibody, 369A has been described previously (Buxbaum et al., *Proc. Natl. Acad. Sci. USA*, 87, 6003–6006, 1990). Agarose-coupled anti-mouse and anti-rabbit secondary antibodies were purchased from HyClone Laboratories, Inc. (Logan, Utah). Protein A Sepharose CL-4B (PAS) was obtained from Pharmacia LKB.

EXAMPLE 1

Undifferentiated PC12 cells were grown to confluency on three 10 cm diameter culture dishes in Dulbecco's modified Eagle's medium containing 10% (vol/vol) heat-inactivated fetal bovine serum, 5% (vol/vol) heat-inactivated horse serum, and antibiotic-antimycotic solution (Gibco) at 37° C (all subsequent incubations up until cell lysis were performed at this temperature) and 5% C02. Cells were washed twice with Hepes-buffered saline (HBS) (10 mM Hepes, pH 7.4/110 mM NaCl/5 mM KCl/2 mM CaCl2/1 MM MgSO41, suspended in HBS, and pelleted by brief centrifugation. The cells were resuspended in 1 ml of methionine-free Eagle's modified minimum essential medium (MEM) containing 25 mM Hepes, pH 7.4. After a 45 min preincubation, cells were pulse-labelled for 20 min by the addition of 1 mCi of [$^{35}$S]methionine (1000 mCi/mmol; NEN Research Products). The chase period was initiated by the addition of 5 ml of MEM containing excess unlabeled methionine (200 $\mu$M) and 25 mM Hepes, pH 7.4, and aliquoting of 200 $\mu$l samples to microcentrifuge tubes.

When chloroquine (50 $\mu$M) was used, drug was added at the start of the chase period. When the effects of monensin (10 $\mu$M) or brefeldrin A (10 $\mu$g/ml) were examined, drug was added at the start of the preincubation period and was present throughout the pulse-chase. Cell viability remained unchanged throughout the chase period as determined by trypan blue exclusion.

At the end of the chase period (0–8 h), cells were rapidly pelleted and the medium removed. Cells and medium were treated with 1% (wt/vol) sodium dodecyl sulfate (SDS), boiled 5 min, sonicated (cell lysates only), and centrifuged at 10,000×g for 10 min. After dilution with an equal volume of neutralization buffer [6% (vol/vol) Nonidet-P40/200 niM Tris, pH 7.4/300 mM NaCl/10 mM EDTA/4 mM NaN3], supernatants were incubated at 40° C. with antibody 22C11 overnight (medium) or with antibody 369A for 2 h (cell lysates). Immune complexes were precipitated with 200 $\mu$l (vol/vol) of agarose-coupled anti-mouse or anti-rabbit antibody or with PAS, and the pellets washed three times with 1 ml of Tris-buffered saline [100 mM Tris, pH 7.4/150 mM NaCl/2 mM NaN3].

Samples were boiled in 100 $\mu$l of sample buffer [62.5 mM Tris, pH 6.8/2% SDS/5% 2-mercaptoethanol/10% sucrose] and separated by SDS polyacrylamide gel electrophoresis on 4-15% gradient gels (cell lysates) or 6% gels (medium). Gels were treated for fluorography with enhancer solution (Entensity; N-EN Research Products) and exposed to preflashed x-ray film at −70° C. Proteins were quantitated by scanning densitometry (since immature APP$_{751}$ and APP$_{770}$ isoforms could not be resolved by densitometry, they are reported together as immature APP$_{KPI}$). Values were corrected for length of exposure time, signal decay, and the number of methionine residues in individual APP species, and normalized to the total APP holoprotein present in untreated cells at the start of the chase period (100 relative units). Statistical significance was determined using Student's unpaired t-test.

Identification of APP species. When APP was immunoprecipitated from metabolically-labelled PC12 cells using an antibody directed against the carboxyl terminus of APP, six protein bands of molecular masses 106, 112, 116, 125, 139, and 146 kDa were identified (FIG. 1B). The three lower bands have previously been designated as immature APP$_{695}$, APP$_{751}$, and APP$_{770}$ holoprotein, respectively, and the three higher bands as the corresponding mature APP isoforms, in which the proteins are fully N- and O-glycosylated and sulfated (13, 20). Using agents that inhibit conversion of immature to mature APP (see below) and a monoclonal antibody directed against a Kunitz semine protease inhibitor (KPI) domain of isoforms APP$_{751}$ and APP$_{770}$, and based upon the lengths of the individual isoforms, the protein band assignment was confirmed.

Also present in the immunoprecipitated cell lysates was a protein of molecular mass 16.3 kDa (FIG. 1C). (This APP species comigrated with the alpha-lactalbumin standard marker that has a reported molecular mass of 14.2 kDa; however, when the molecular mass of the APP species was determined by linear regression analysis as was done for the APP holoproteins, the molecular mass was calculated to be 16.3 kDa; for consistency, the molecular mass will be reported as 16.3 kDa.) This truncated APP fragment represents the carboxyl terminal product resulting from the normal intra-amyloid cleavage of APP as determined by its protein sequencing. Immunoprecipitation of the seven APP species with the carboxyl-terminal antibody could be abolished by preincubation of antibody with peptide corresponding to $App_{645-694}$ ($APP_{695}$ numbering system).

When culture medium was immunoprecipitated with antibody directed against the amino terminus of APP, three protein bands of molecular masses 109, 123, and 129 kDa were identified (FIG. 1D). The two higher bands could also be immunoprecipitated with the antibody directed against the KPI domain insert. These proteins could not be immunoprecipitated with the anti-carboxyl terminal antibody. Since the difference in masses between the mature APP holoproteins (from which the secreted forms are believed to arise; see below) and the APP carboxyl-terminal fragment closely agree with the masses of the secreted forms, it was concluded that they are the secreted fragments of $APP_{695}$, $APP_{751}$, and $APP_{770}$. No secreted forms could be recovered from cell lysates when supernatants from immunoprecipitations with anti-carboxyl terminal antibody were re-incubated with anti-amino terminal antibody.

Effect of chlorocuine on acidic oroanelles. Since evidence for lysosomal APP processing has been reported previously, the effects of chloroquine on APP metabolism were examined. Chloroquine is a weak base that is taken up by cells where it is concentrated iii-and neutralizes acidic organelles such as lysosomes. The elevated pH of these organelles results in the inhibition of their acid-dependent hydrolases. Chloroquine neutralization of acidic organelles was confirmed by fluorescence microscopy of acridine orange-treated cells in the absence and presence of chloroquine.

Effect of chlorocuine on APP maturation. At the start of the chase period nearly all of the labelled APP was in the form of immature holoprotein (FIG. 1B). Within approximately 15 min, half of the immature APP was converted to mature APP (FIG. 2). No difference in the rate of maturation was found between $APP_{695}$ and APPKPI-Chloroquine had virtually no effect on APP maturation (FIG. 2).

Effect of chlorocuine on mature APP holoprotein. In untreated cells, the level of mature APP holoprotein rose to a maximum by 30 minutes, corresponding to conversion of immature APP to its fully glycosylated and sulfated form (FIG. 3). The amount of mature APP isoforms then decreased with a half-life of about 90 min. At 8 hours of chase, the levels of mature APP isoforms had reached their starting levels. The decrease of APP levels with time was attributed to conversion of mature APP to secreted forms as well as to proteolytic degradation unassociated with secretion.

When cells were treated with chloroquine, a significant effect on turnover of mature APP was observed (FIG. 3). The levels of mature APP holoprotein peaked 30 minutes later than in control samples. APP isoforms were present at approximately twice the levels found in untreated cells, from 1 to 8 hours of chase. The magnitude of the chloroquine effect was the same for the different APP isoforms.

Effect of chlorocuine on APP secretion. In untreated cells, after a brief lag, levels of secreted APP isoforms rose linearly from 0 to 4 hours of chase (FIG. 4). Little or no further increase in APP secretion was observed up to 8 hours of chase. Maximal levels of secreted APP represented about 14% of total APP present at the start of chase.

When cells were treated with chloroquine, virtually no change in the rate of APP secretion was found for any APP isoform (FIG. 4). The maximal level of APP secretion was approximately the same for control and chloroquine-treated samples at 4 hours. At 6 and 8 hours of chase, there was a small decrease in recovered secreted APP when chloroquine was present. This decrease was attributable to proteolytic degradation in the medium, since recovery of secreted APP in 4 hours chase medium incubated in the absence of cells decreased with time. Chloroquine was found to catalyze the proteolysis in the medium to an extent comparable to that shown in FIG. 4.

Effect of chlorocuine on APP C-terminal fragment. In untreated cells, the level of the APP carboxyl-terminal fragment reached a maximum at 1 hours of chase and decreased slowly thereafter (FIG. 5). As mature APP holoprotein was still being degraded, and secreted APP was still being produced at this time, it is concluded that the carboxyl-terminal APP fragment is subject to further proteolytic degradation.

Chloroquine had a significant effect on recovery of the carboxylterminal fragment. The maximal amount of 16.3 kDa APP was found at 4 hours of chase. Thereafter, the level of APP fragment decreased at a rate equal to that observed in untreated cells. These data are consistent with the APP carboxyl-terminal fragment being further degraded in an acidic organelle following cleavage.

The maximal level of APP fragment was equivalent to approximately 9% of APP holoprotein present at the start of chase and 60% of total secreted APP (in terms of relative units, which have been corrected for the number of methionine residues; see above). In the presence of chloroquine, these values were 13% and 92%, respectively.

EXAMPLE 2

Effects of ammonium chloride, monensin and brefeldin A on APP processing. In addition to chloroquine, the effect of the lysosomotropic agent ammonium chloride (50 mM) on APP processing was examined. Ammonium chloride exhibited effects on APP turnover similar to those of chloroquine. However, it had a strong inhibitory effect on APP maturation. Because of its complicated effects, ammonium chloride was not further examined.

The monovalent cation ionophore monensin disrupts proton gradients and thereby alkalinizes acidic organelles including lysosomes and the trans Golgi. When monensin was added at the start of chase, it inhibited APP turnover to an extent similar to that observed with chloroquine and ammonium chloride. When monensin was present from the beginning of the preincubation period and throughout the pulse-chase period, it completely inhibited APP maturation (FIG. 6A). Furthermore, no 16.3 kDa APP fragment or secreted APP fragment was recovered (FIGS. 6B and 6C).

The fungal product brefeldin A produces an apparent dissolution of the Golgi complex by causing resorption of the cis/medial Golgi into the endoplasmic reticulum. When cells were treated with brefeldin A from the start of the preincubation period, normal APP maturation was inhibited (FIG. 6A). Instead, a broad band of molecular mass greater than immature APP but less than mature APP was observed. As cis/medial Golgi enzymes, though relocated to the endoplasmic reticulum, can still function in the presence of brefeldin A, it is probable that APP underwent abnormal glycosylation. Brefeldin A also prevented secretion of APP fragments and production of the carboxyl-terminal fragment (FIG. 6B and 6C).

What is claimed is:

1. A method of modulating or affecting the intracellular trafficking and processing of APP in the mammalian cell of a patient in need of therapy for amyloidosis associated with Alzheimer disease thereby inhibiting production of Alzheimer type amyloidosis which comprises administration to a mammal in need of such therapy an effective amount of an agent which modulates or affects the intracellular trafficking of proteins in the mammalian cell.

2. A method according to claim 1 wherein the agent is chloroquine.

3. A method according to claim 1 wherein the agent is monensin.

4. A method according to claim I wherein the agent is brefeldin A.

5. A method of treating amyloidosis associated with Alzheimer disease in a mammalian patient in need of such therapy comprising administering to the patient an effective amount of at least one agent capable of modulating or affecting the trafficking and processing of APP in the mammalian cell.

6. A method according to claim 5 wherein the agent is chloroquine.

7. A method according to claim 5 wherein the agent is monensin.

8. A method according to claim 5 wherein the agent is brefeldin A.

* * * * *